(12) United States Patent
Hamann et al.

(10) Patent No.: US 8,718,939 B2
(45) Date of Patent: May 6, 2014

(54) METHOD AND APPARATUS FOR THREE DIMENSIONAL DYNAMIC MEASUREMENTS IN WATER SYSTEM

(75) Inventors: Hendrik F. Hamann, Yorktown Heights, NY (US); Levente I. Klein, Tuckahoe, NY (US); Andriy Stepanchuk, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 269 days.

(21) Appl. No.: 13/074,243

(22) Filed: Mar. 29, 2011

(65) Prior Publication Data
US 2012/0253673 A1    Oct. 4, 2012

(51) Int. Cl.
*G01V 3/00* (2006.01)
*G01V 7/00* (2006.01)

(52) U.S. Cl.
USPC ............................. 702/2; 367/131; 367/135

(58) Field of Classification Search
USPC ....................................... 702/2; 367/131, 135
See application file for complete search history.

(56) References Cited

U.S. PATENT DOCUMENTS

| | | | |
|---|---|---|---|
| 5,126,978 A * | 6/1992 | Chaum ......................... | 367/135 |
| 5,568,450 A | 10/1996 | Grande et al. | |
| 6,002,644 A * | 12/1999 | Wilk ............................. | 367/88 |
| 6,820,008 B1 * | 11/2004 | van Smirren et al. ............. | 702/2 |
| 7,040,157 B2 * | 5/2006 | Glasgow et al. ........... | 73/170.29 |
| 7,353,113 B2 * | 4/2008 | Sprague et al. ................... | 702/2 |
| 7,603,251 B1 * | 10/2009 | Wiegert et al. ................ | 702/152 |
| 2005/0251339 A1 * | 11/2005 | Araki et al. ....................... | 702/2 |
| 2008/0061790 A1 * | 3/2008 | Strack ............................ | 324/336 |
| 2009/0265111 A1 * | 10/2009 | Helwig et al. ..................... | 702/7 |

FOREIGN PATENT DOCUMENTS

| | | |
|---|---|---|
| CA | 2547359 A1 | 6/2005 |
| CA | 2554215 A1 | 6/2005 |
| WO | 2009045109 A1 | 4/2009 |
| WO | 2009/093766 A1 | 7/2009 |

OTHER PUBLICATIONS

P. Jiang, "Design of a Water Environment Monitoring System Based on Wireless Sensor Networks", Aug. 19, 2009, Sensors, vol. 9, pp. 6411-6434.*

(Continued)

*Primary Examiner* — John Breene
*Assistant Examiner* — Stephanie Bloss
(74) *Attorney, Agent, or Firm* — Vazken Alexanian; Ryan, Mason & Lewis, LLP (57) ABSTRACT

Techniques for measuring one or more physical properties of a water system. A measurement platform is positioned at a first location of a given water system, wherein the measurement platform comprises a plurality of sensor devices distributed over a three dimensional space and configured to acquire data relating to one or more physical properties of the water system. A first set of measurement data is acquired from the water system at the first location via at least a portion of the plurality of sensor devices of the measurement platform. The measurement platform is moved along a predetermined path to at least a second location in the water system. At least a second set of measurement data is acquired from the water system at the second location via at least a portion of the plurality of sensor devices of the measurement platform.

22 Claims, 8 Drawing Sheets

(56) References Cited

OTHER PUBLICATIONS

A. Weckenmann et al., "Multisensor Data Fusion in Dimensional Metrology," CIRP Annals—Manufacturing Technology, 2009, pp. 701-721, vol. 58, No. 2.

V.A. Bell et al., "Using a 1-D Mixing Model to Simulate the Vertical Flux of Heat and Oxygen in a Lake Subject to Episodic Mixing," Ecological Modelling, Jan. 2006, pp. 41-54, vol. 190, Nos. 1-2.

Geoff Bohling, "Kriging," C&PE 940, Oct. 2005, 20 pages.

* cited by examiner

METHOD AND APPARATUS FOR THREE DIMENSIONAL DYNAMIC MEASUREMENTS IN WATER SYSTEM

FIELD OF THE INVENTION

The present invention relates to measurements of physical properties of a water system, and more particularly to a three dimensional sensor grid for providing such measurements and techniques for using same.

BACKGROUND OF THE INVENTION

Water systems such as rivers, lakes, and ponds can be highly dynamic systems where the volume may change in a time frame that can be from minutes to years. Changes in the water volume also have a strong influence on the system's physical parameters that change both over space and time. In the case of external disturbances such as rain, storms or drought, the physical parameters of water can change by orders of magnitude compared with values measured under normal conditions. These perturbations can result in a change in the physical parameter of the water system, such as turbidity and dissolved oxygen, and they can also pose stress on the living organism in the water system.

Existing practices in water monitoring are based on the acquisition of water samples once or twice per day that are analyzed in a laboratory with analysis results being available within days or weeks. While these laboratory analysis methods are accurate and well established, the obtained results with regard to composition and quality of the monitored water system only give a snapshot of the water system at the time the measurements were taken, i.e., days or weeks in the past.

Furthermore, the total number of sampling points of the water system is scarce due to the use of manual acquisition of the samples. This makes the correlation of quality and composition of acquisition points difficult due to reduced sampling points.

Simulations/modeling of the water system is possible, however, the lack of real time data makes the outcome difficult to verify.

SUMMARY OF THE INVENTION

Illustrative embodiments of the invention provide techniques for measuring one or more physical properties of a water system.

For example, in one embodiment, a method comprises the following steps. A measurement platform is positioned at a first location of a given water system, wherein the measurement platform comprises a plurality of sensor devices distributed over a three dimensional space and configured to acquire data relating to one or more physical properties of the water system. A first set of measurement data is acquired from the water system at the first location via at least a portion of the plurality of sensor devices of the measurement platform. The measurement platform is moved along a predetermined path to at least a second location in the water system. At least a second set of measurement data is acquired from the water system at the second location via at least a portion of the plurality of sensor devices of the measurement platform.

The method may further comprise feeding the individual data sets into physical models to create three dimensional maps of the variation of the physical parameters. Furthermore, the method may further comprise generating an image based on the first set of measurement data and the at least a second set of measurement data, wherein the image represents the one or more physical properties of the water system.

Advantageously, illustrative embodiments of the invention provide techniques for obtaining real-time measurements and analysis of water systems.

These and other objects, features, and advantages of the present invention will become apparent from the following detailed description of illustrative embodiments thereof, which is to be read in connection with the accompanying drawings.

DETAILED DESCRIPTION OF PREFERRED EMBODIMENTS

Illustrative embodiments of the invention may be described herein in the context of certain types of water systems and measurement of certain properties or parameters of such water systems. However, it is to be understood that the techniques of the invention are not necessarily limited to use in any particular type of water system, or for measurement of any particular properties or parameters, but are more broadly applicable to any suitable type of liquid or fluid system for the measurement of any suitable properties or parameters.

It is realized that high resolution data acquisition enables data display and observation of a given parameter distribution both in space and time. For example, where the water system is a pond, the temperature distribution in the pond would vary from the shore to the center of the pond with additional significant variations from the top of the pond down to the bottom. Furthermore, the temperature distribution of the water system would also be affected by periodic temperature variation that occurs during the course of the day, e.g., from a warm sunny day to a cold night. The presence of light/radiation from the sun would further modify the biological and chemical processes in the water system like pH or dissolved oxygen.

While mathematical models may exist to describe various parameter changes in the water system, every single water system has a unique environment making its specific description difficult without reliable measurement data. Given that water systems are very dynamic and correlated systems, i.e., one parameter change may change other parameters instantly, existing mathematical methods may not capture these subtle effects. In a controlled water system, the connection between different parameters may be understood, but such connections and correlations are unknown in the field and not easily determinable in other water systems such as ponds, lakes, etc. Attaining knowledge and a full understanding of all parameters and their interconnections and correlations, and their response to external stimulus, is highly desired.

Accordingly, to overcome the above-mentioned drawbacks as well as other drawbacks of existing approaches, illustrative embodiments of the invention provide measurement systems and methods that measure temporal and three dimensional spatial variations of a water system using high density data acquisition both in space and time. The acquired data can be used to develop models, calibrate existing models and constrain the physical models for the water system. For all these purposes, a three dimensional distribution of data on a well defined grid can be used to integrate such measurements into physical models. Furthermore, a distribution of static sensors positioned in locations of interest could monitor the temporal variations associated with the water system. The temporal variation can be used to corroborate the long term prediction of the models with measurement data to detect when models developed based on spatial variation data changed in time and have to be rerun for real time assessment of the water system.

For example, in one illustrative embodiment, a methodology is provided to acquire high resolution and densely distributed data in a water system such as a pond, lake, ocean, shore, or river. The methodology employs a mobile sensor grid platform that scans the water system while having a distribution of sensors extending in all three directions (dimensions) of the space. The data acquisition points are distributed on a grid, and a sequence of data from a single or multiple sensors in a single spatial location are acquired and stored. Once the measurement is performed, the sensor platform is moved to a new location in the water system, and measurement data is acquired at the new location.

Covering the entire area of the water system, this approach allows a three dimensional data sampling of relevant parameters in the water system including, but not limited to, temperature, pH, turbidity, dissolved oxygen, etc. The stored data is used for visualizing the distribution of physical parameters extending in all three directions of space. That is, one or more images representing the physical properties or parameters may be generated for presentation on a display to a person or persons interested in the properties of the water system being monitored. Examples of such images will be given below.

Furthermore, the stored data can be integrated in physical models to describe the state of the water system and, still further, used to predict its time evolution based on external events such as, but not limited to, storms, rainfalls, flooding, or pollution. For example, in one of many simulations, lakes can be assumed as a two layer system where the top layer can be assumed to be well mixed and homogeneous with no temperature variation across this layer, while the lower part of the lake can be assumed to be stratified where the temperature is varying following a polynomial distribution. These models are used in many simulations to predict how water gets mixed and can be used to estimate the sediment distribution, oxygen, heat and pollutants. A common problem with these types of models though is that they are one dimensional and one could not capture any spatial variation that can be associated with the variable depth of lakes or rivers. The inventive measurement system described herein can measure the temperature variations in the water system to calibrate the model and determine how the parameters of the model are changing spatially. One example of such a model is described in V. A. Bell et al, "Using a 1-D Mixing Model to Simulate the Vertical Flux of Heat and Oxygen in a Lake Subject to Episodic Mixing," volume 190, issues 1-2, 10 Jan. 2006, pages 41-54, Ecological Modeling, the disclosure of which is incorporated by reference herein.

Establishing baseline models of the water system and distribution of the physical parameters that characterize such systems is beneficial to characterize temporal changes that are beneficial to control and to monitor the quality of the water system so as to optimize process performance and reduce operational cost. For example, in the case of pollution, pollutants can be neutralized but the amount of neutralizing agents (chemicals) that have to be added and the location of where to expedite the dissolving and transport of the neutralizing agents across the water body should be determined. These parameters can be determined using techniques of the present invention. Another example is in the case of a water supply. For a water supply system where water is extracted both from surface collection bodies such as lakes and also from the ground storage in a well-defined ratio situation, it may occur that one water source is not adequate. For example, when the surface water turbidity level is too high as determined by the inventive measurement system, the entire demanded supply can be extracted from the ground until the surface water quality becomes suitable to complement the ground water. The measurement of the water quality level, using techniques of the present invention, allows for optimizing and adjusting pricing models, for example, the cost of technology to adjust the surface water conditions versus the price of ground pumping that is more energy intensive and also may deplete the underground water supply.

Figure 1A:
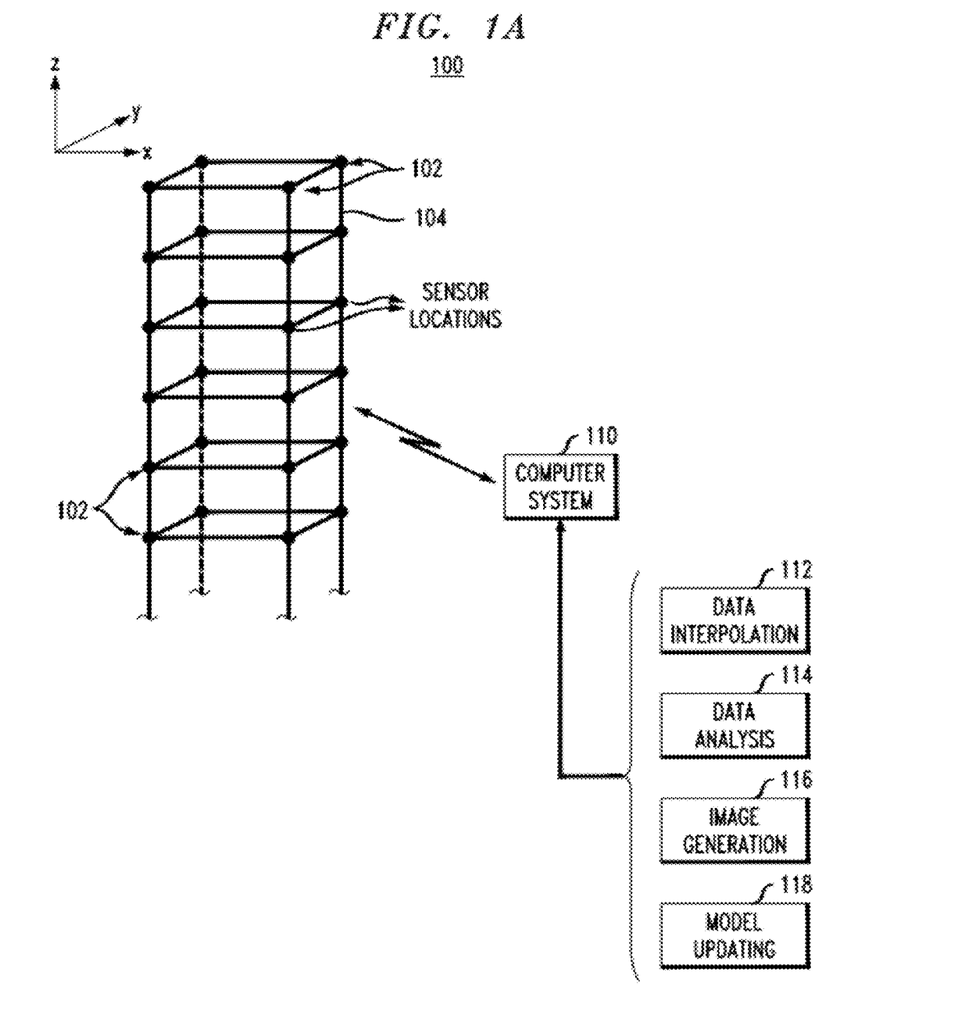
FIG. 1A illustrates distribution of sensors on a grid for three dimensional measurements of physical parameters, according to an embodiment of the invention.

FIG. 1A illustrates distribution of sensors on a grid (more generally, platform) 100 for three dimensional measurements of physical parameters of a water system, according to an embodiment of the invention. As shown, the grid 100 comprises a plurality of sensors 102 situated on a frame 104 at various three dimensional points on the grid 100. Each dot on the grid 100 in FIG. 1A is considered a sensor. Note that the coordinate x-y-z axis shown next to the grid represents the three dimensional space. Thus, in the case where the grid is placed in a selected portion of a pond (by way of example), the sensors 102 distributed in the x-direction would measure properties of the pond over a predetermined width of the selected portion of the pond in which the grid resides, while the sensors 102 distributed in the y-direction would measure properties of the pond over a predetermined length of the selected portion of the pond, and the sensors 102 distributed in the z-direction would measure properties of the pond over a predetermined depth of the selected portion of the pond. Measurement data can be transmitted (wireline or wireless) from the sensors to a computer system 110 for further processing such as, for example, data interpolation 112, data analysis 114, image generation 116, model updating 118, as will be explained below. Furthermore, the platform grid 100 may include local memory (not shown) for storing measurements obtained by the sensors. The data stored locally can then be transmitted or obtained at a later time.

Once data is acquired by all or a selected subset of the sensors 102 at the selected portion of the pond (first location), the grid 100 is moved to a next selected portion of the pond (next location) to acquire a next set of data.

It is to be understood that the types of sensors that constitute sensors 102 depend on the water system being measured and the properties or parameters sought to be measured. For example, each sensor 102 could be configured to read one or more physical properties or of parameters of the water system such as, but not limited to, temperature, pH, turbidity, and dissolved oxygen. Thus, examples of sensors include, but are not limited to, pH sensors, conductivity sensors, dissolved oxygen sensors, temperature sensors, turbidity sensors, oxygen content sensors, nitric oxide sensors, and phosphorus sensors. There are a wide variety of these sensors and they are commercially available from suppliers such as, by way of example, PGC Scientifics (Palm Desert, Calif.) and Cole Palmers (Vernon Hills, Ill.). Such commercially-available sensors can be integrated in a measurement system of the invention including a platform grid (e.g., as shown in FIG. 1A) to acquire data points at predefined positions. The data points can be stored locally and retrieved at a later time or they can be transmitted wirelessly to a computer that is positioned near the shore.

As shown, the sensors 102 are considered data point locations and are situated on the frame 104 of the grid 100. Frame 104 can be constructed from any suitable material including, but not limited to, any plastic, metal or wood material (or combinations thereof) that allows the sensors to be attached thereon and would permit the sensors to be fixed at a given height and position with respect to other sensors.

Figure 1B:
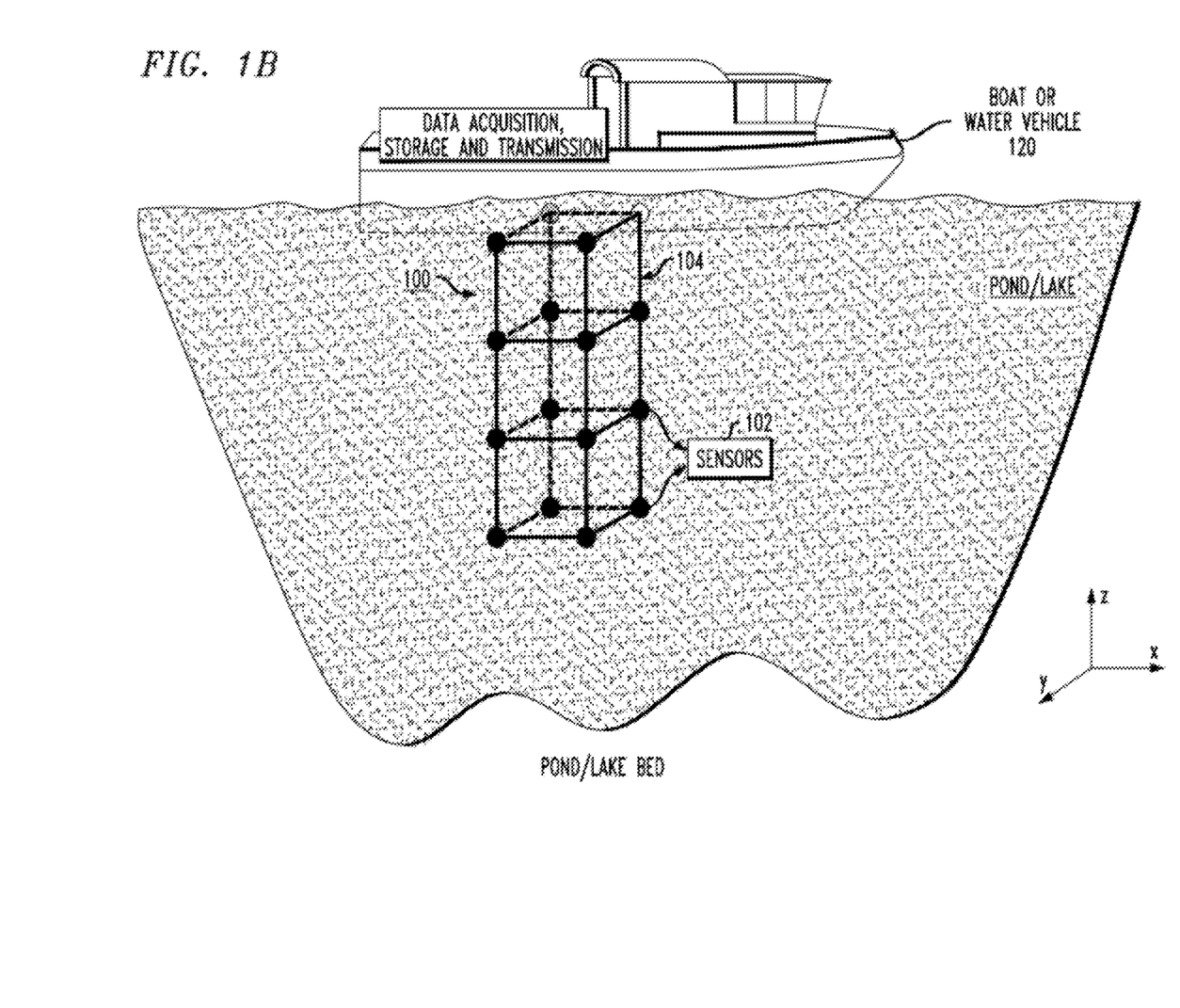
FIG. 1B illustrates distribution of sensors on a grid attached to the bottom of a boat, according to an embodiment of the invention.

In one embodiment, the frame 104 of the grid 100 to which the sensors 102 are secured (e.g., via clamping, gluing, wiring, screwing, etc.) can be attached to the bottom of a boat 120 shown in FIG. 1B that moves along a predetermined path on the surface of the water system. Alternatively, the grid can be attached to a submersible vehicle enabling a measurement at greater depths below the surface of the water system.

Figure 2A:
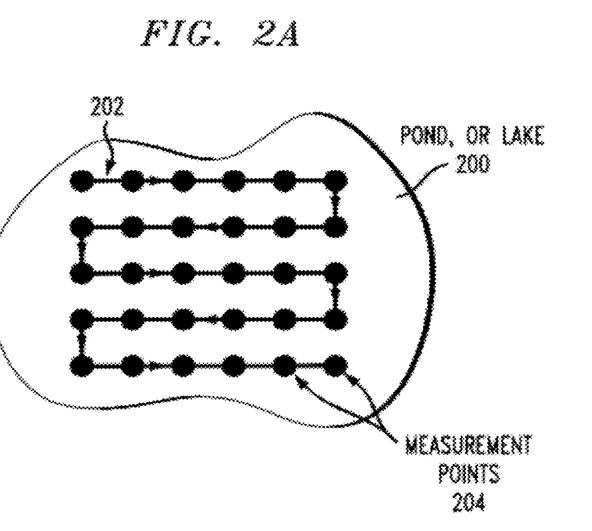
FIG. 2A illustrates a predetermined path through which a grid of sensors is moved in a pond/lake based water system, according to an embodiment of the invention.
Figure 2B:
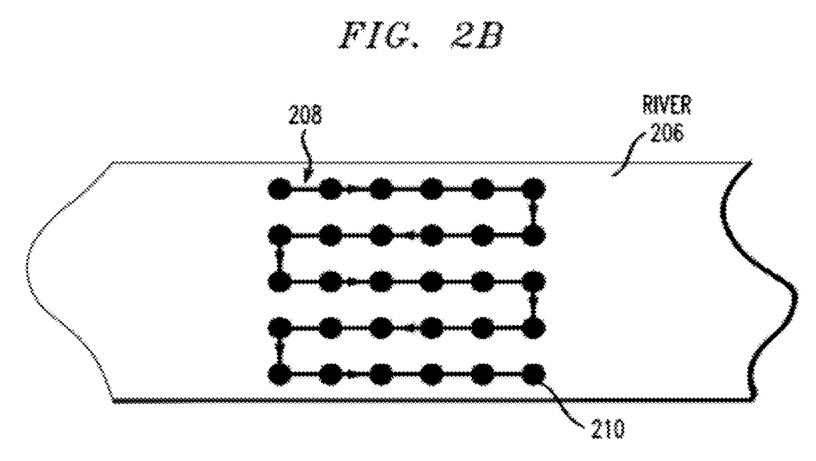
FIG. 2B illustrates a predetermined path through which a grid of sensors is moved in a river based water system, according to an embodiment of the invention.

FIG. 2A illustrates a predetermined path through which a grid of sensors is moved in a pond/lake based water system, while FIG. 2B illustrates a predetermined path through which a grid of sensors is moved in a river based water system. That is, for scanning the water system (200 in FIG. 2A and 206 in FIG. 2B), the boat/submersible vehicle can follow a well-defined path (202 in FIG. 2A and 208 in FIG. 2B). Note that the direction of the path is depicted by the direction of the arrows in the figure.

Orderly distributed points are positioned on a two dimensional grid. These points are represented in FIGS. 2A and 2B as measurement points 204 and 210, respectively. Each measurement point represents a location where the sensor platform is positioned and measurement data is acquired. At every point (204 or 210), measurement data for one or more physical parameters can be acquired and stored in a storage medium for further processing. For example, as a further processing step, the measurement data is assembled in an image with data points populating the grid of points.

Figure 2C:
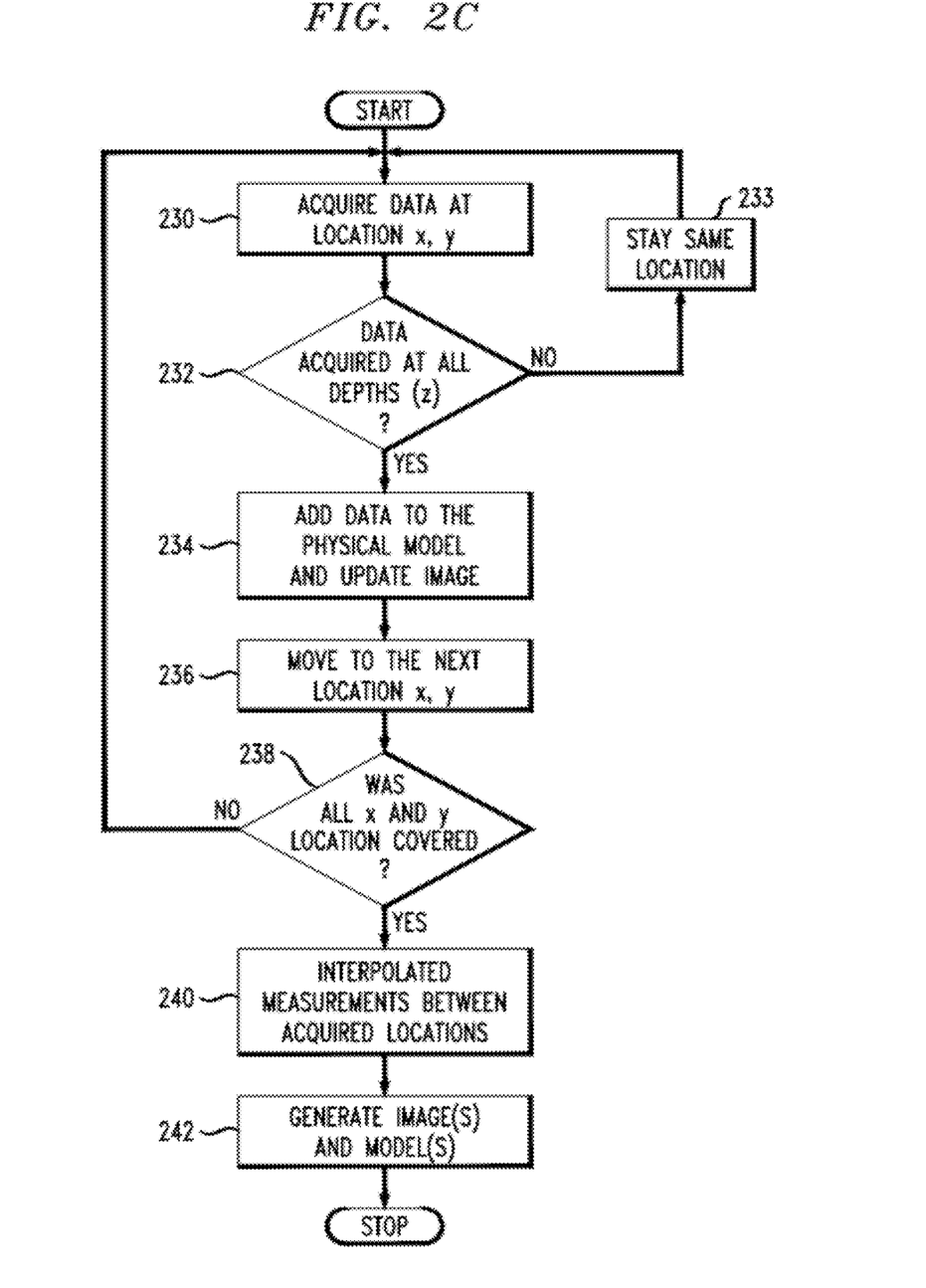
FIG. 2C is a flow diagram illustrating the process shown in FIGS. 2A or 2B, according to an embodiment of the invention.

FIG. 2C is a flow diagram depicting the acquiring of data along the predetermined path through which a grid of sensors is moved in a pond/lake or river-based water system as shown in FIGS. 2A and 2B. In step 230, the grid 100 is positioned at a first location (x, y) wherein the sensors acquire data at all desired depths (z) (step 232). Step 233 provides for iterating at the current position until data is acquired at all depths. Data acquired is added in step 234 to the physical model and the images are updated. In step 236, the grid 100 is moved to the next location x, y for which data is acquired at all desired depths (z). Step 238 determines whether all locations in the predetermined path have been covered. Data is acquired at all locations x, y until all locations have been covered. Once all data has been acquired, the measurements are interpolated between the acquired locations in step 240 and one or more images and one or more models (one or more updated models and/or one or more new models) are generated in step 242.

Figure 5A:
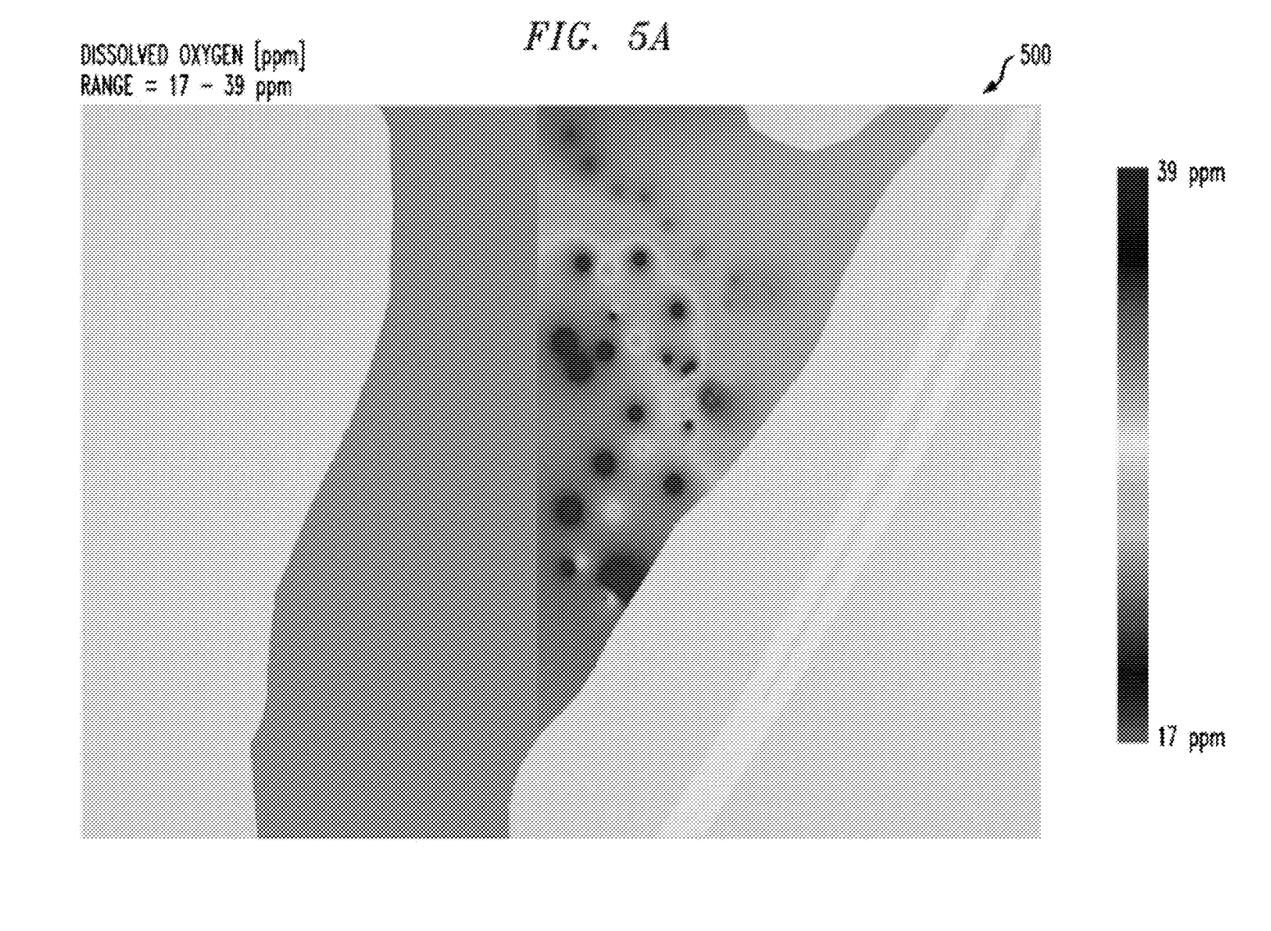
FIG. 5A illustrates a first example image generated in accordance with one or more embodiments of the invention.
Figure 5B:
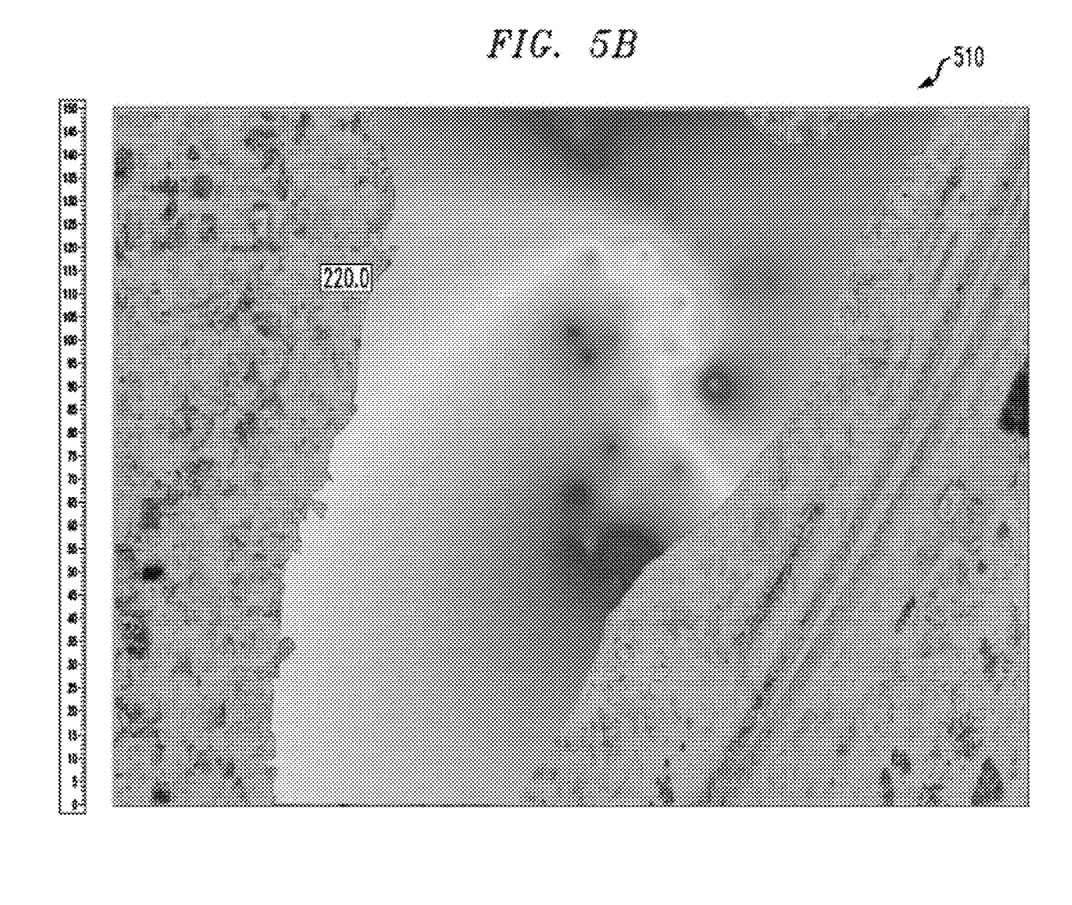
FIG. 5B illustrates a second example image generated in accordance with one or more embodiments of the invention.

FIGS. 5A and 5B show examples of such generated images. The images were acquired by attaching a platform grid 100 with water multisensory capability (i.e., multiple sensors that measure parameters associated with a water system) to a robotized boat that was programmed to scan the surface of a given lake. Measurement data was acquired at predefined points on the lake with the boat moving from one location on the predetermined path to the next location. The data is acquired on a well-defined grid and images are generated by extending the measured value from point to point using well-known extrapolation techniques. For example, in image 500 in FIG. 5A which illustrates dissolved oxygen levels (in parts per million) in the subject lake, the data points where measurements were taken are assumed to be the measured values, which decrease as the measurement point is departed. To accommodate the various measurement values, the data is extrapolated between measurement points based on physical relationships that take into account variations as, for example, diffusion models for temperature or dissolved oxygen variations, see also, e.g., image 510 in FIG. 5B.

Figure 3A:
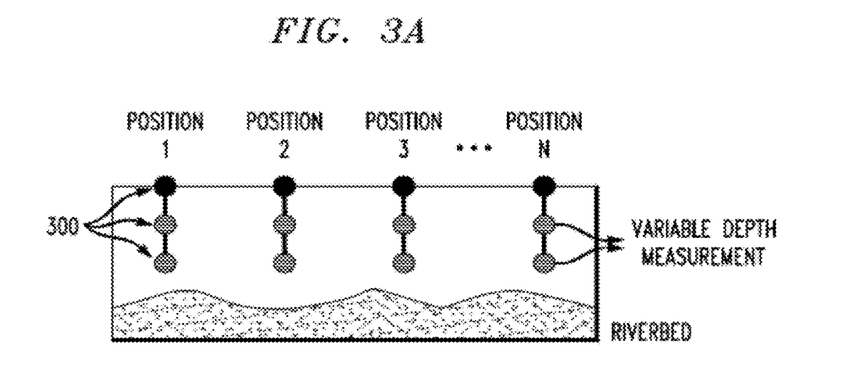
FIG. 3A illustrates extension in a third dimension of measurement through a set of sensors positioned at different depths, according to an embodiment of the invention.
Figure 3B:
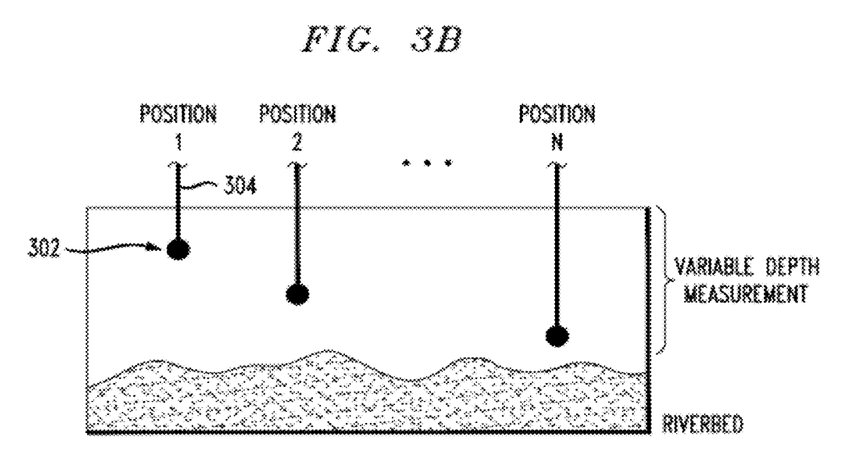
FIG. 3B illustrates extension in a third dimension of measurement through lowering a sensor to different depths by using an extending pole, according to an embodiment of the invention.

Furthermore, in illustrative embodiments, variable depth data acquisition can be achieved through various approaches. In a first approach, as shown in FIG. 3A, sensors 300 are situated at variable depths, and the group of sensors are moved to different positions (position 1, . . . , position N) at which measurement data is acquired. In a second approach, as shown in FIG. 3B, a sensor 302 is positioned at the end of an extending pole 304 and it is lowered to variable depths for measurement at different positions across the surface of the water system (position 1, . . . , position N). The extending pole can be controlled by a motorized engine (not shown) that extends the pole to a certain depth in the water system with the sensor attached to the end of the pole. The extending pole and sensors can be considered a measurement platform or part of a measurement platform (e.g., such as platform 100).

Figure 3C:
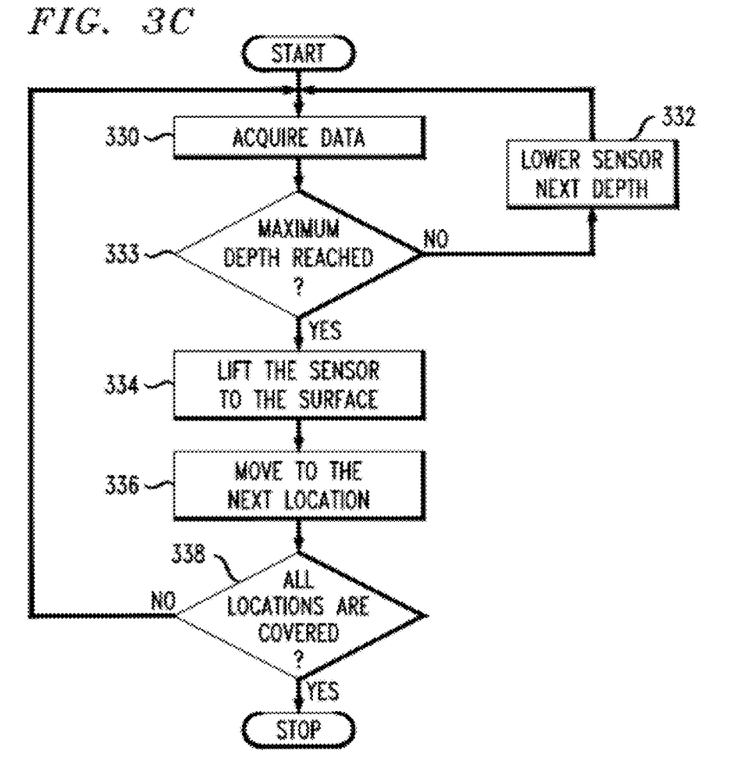
FIG. 3C is a flow diagram illustrating the process shown in FIG. 3B, according to an embodiment of the invention.

FIG. 3C is a flow diagram depicting the variable depth measurement shown in FIG. 3B. In step 330, data is acquired first with the sensor at a depth closest to the surface. The sensor is then lowered to the next depth (step 332) and again data is acquired. The process continues until the maximum depth has been reached (step 333) at which point the sensor is lifted to the surface (step 334) and moved to the next location (step 336). The process is repeated until all desired locations are covered (step 338).

The water system scanning is achieved by controlling, for example, the engine of the boat through computer commands to move the boat to well-defined locations and cover the entire surface of the water system. As the boat reaches the point of interest that has been preprogrammed, the sensor platform is stopped at predefined points and measurements are performed at variable depths.

Both the locations of the sensors (all three dimensions) and the measured physical parameters are recorded at a location. The measurement process proceeds by positioning the sensor platform at a starting point and acquiring data, then moving to the next point and acquiring the data, all while following a well-defined path.

The locations of the sensor platform can be determined by localization using a set of sensors (acoustic, visual etc) positioned at the edge of the water system that track position and location or using a general GPS (global positioning system) system. The typical accuracy of the GPS system is about 10 feet, and for situations where a more precise localization is required, either global or local landmarks can be used. The data is acquired on a computer (110 in FIG. 1) attached to the sensor platform that records both position and measurement data at every location. In one embodiment, the data can be transmitted wirelessly to the host computer. In such a case, each sensor can have wireless data transmit/receive capability.

The stored data on the sensor platform can be used for further processing to map out the spatial distribution of physical parameters such as temperature or dissolved oxygen variation in the pond system.

One advantage of having data points on a well-defined grid is the ability to interpolate the physical parameters between two points in the system to establish the physical parameters. The interpolation of data based on sparse measurement points is highly effective in the case of well defined measurements points based on a three dimensional grid. Some of the numerical techniques that can be used for interpolation are the inverse distance interpolation or kriging. "Kriging" is a geostatistical technique for interpolating the value of a random field (e.g., the elevation, z, of the landscape as a function of the geographic location) at an unobserved location from observations of its value at nearby locations. The methods rely on constructing a minimum error variance linear estimate at a location where the true value is unknown. The main elements used in weighting the kriging are the closeness of the data to the location where the estimate is made and how dense the acquired data set is, see, e.g., G. Bohling, "Kriging," C&PE 940, October 1995, the disclosure of which is incorporated by reference herein in its entirety.

These methods allow modeling the water system and creating high density maps based on reduced number of points taking into account the physical boundary of the water system (shores). The modeled water system can establish the baseline for the water system and its validity can be verified through additional measurements where a second measurement would establish the prediction of the modeling. Since the model is developed based on a reduced number of points and assuming certain types of variations between the measurement points, all these models tend to be limited in their scope and the real validation comes from measuring the water system at a later instance in time and validating the assumptions.

The sensor platform measurement according to the invention that provides a three dimensional visualization of the system can be further enhanced by placing static sensors that would track the water system in time. This temporal variation of a limited number of sensors can be used to update the baseline model and track the changes of the water as external changes perturbing the baseline model. In such case, static sensors do not move and acquire data over time. If there is little change from values measured in such a static condition, it can be assumed that no perturbation occurred and the base model is still valid. If the value changed, then the sensor data and locations of sensors are used as a boundary condition to interpolate the changes across the whole system.

The invention further includes a software system which allows for data processing. In one embodiment, the data from the sensors would be sent from the carrier (e.g., boat) via a wireless link to a computer (see FIG. 1A), which allows for visualizing the data as a function of lateral and depth position. The software system includes interpolation algorithms (linear, bilinear, inverse distance and kriging) to improve the visualization results (e.g., performed in accordance with data interpolation module 112 in FIG. 1A). The software system also allows running analytical services on the data (e.g., performed in accordance with data analysis module 114 in FIG. 1A). For example, the system would generate a visualization of areas above certain ranges, which can be user-specified, thereby indicating, for example, dangerous levels. Other forms of data analysis known to those ordinarily skilled in the art can be included in the software system. Note that the levels/ranges are based on standard tables that are published by various agencies, for example, the pollution levels in lakes and rivers are limited to certain levels. The models establish the levels that are above the recommended levels, for example, in the image 510 shown in FIG. 5B, such a high level is measured in the proximity of the shore where the resistivity is very high.

Accordingly, as has been illustratively described herein, principles of the invention provide a measurement method in water that allows a high density of multiple physical parameter acquisition in all three spatial dimensions. Both sensors at the surface of the water system and extending down in depth are utilized for measurement and multiple parameters can be acquired at a certain point. The data is acquired by sensors that are attached to a platform supported by a water traversing vehicle that can cover a well-defined path on the surface or inside the water and its engines being controlled by computer commands. The three dimensional data is assembled in models (e.g., performed in accordance with model updating module 118 in FIG. 1A) to visualize the three dimensional variations and conditions of the physical systems in the form of one or more generated images (e.g., performed in accordance with image generation module 116 in FIG. 1A).

As will be appreciated by one skilled in the art, aspects of the present invention may be embodied as a system, apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RE, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring again to FIGS. 1-3C, 5A and 5B, the diagrams in the figures illustrate the architecture, functionality, and operation of possible implementations of systems, methods and computer program products according to various embodiments of the present invention. In this regard, each block in a flowchart or a block diagram may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagram and/or flowchart illustration, and combinations of blocks in the block diagram and/or flowchart illustration, can be implemented by special purpose hardware-based systems that perform the specified functions or acts, or combinations of special purpose hardware and computer instructions.

Accordingly, techniques of the invention, for example, as depicted in FIGS. 1-3C, 5A and 5B, can also include, as described herein, providing a system, wherein the system includes distinct modules (e.g., modules comprising software, hardware or software and hardware). By way of example only, the modules may include, but are not limited to, a data acquisition module, a data processing module, an image generation module, a data interpolation module, a model updating module, and a data analysis module. These and other modules may be configured, for example, to perform the steps described and illustrated in the context of FIGS. 1-3C, 5A and 5B.

Figure 4:
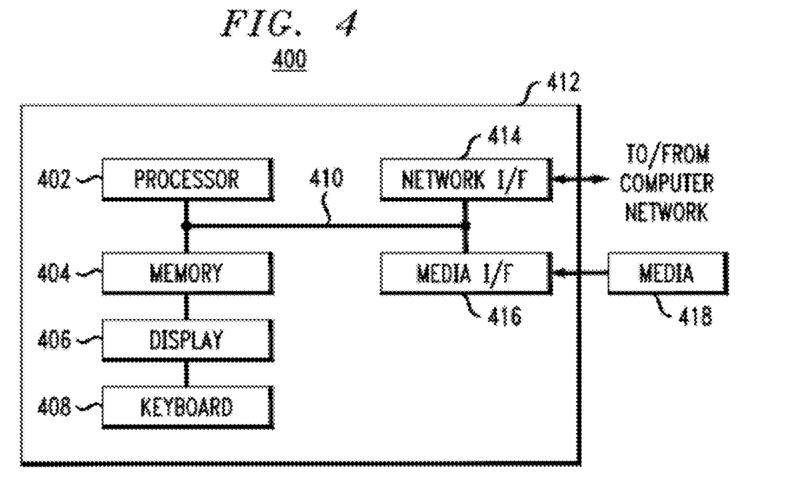
FIG. 4 is a diagram of a computing system for implementing one or more steps and/or components in accordance with one or more embodiments of the invention.

One or more embodiments can make use of software running on a general purpose computer or workstation, e.g., computer system 110 in FIG. 1. With reference to FIG. 4, such an implementation 400 employs, for example, a processor 402, a memory 404, and an input/output interface formed, for example, by a display 406 and a keyboard 408. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, keyboard or mouse), and one or more mechanisms for providing results associated with the processing unit (for example, display or printer).

The processor 402, memory 404, and input/output interface such as display 406 and keyboard 408 can be interconnected, for example, via bus 410 as part of a data processing unit 412. Suitable interconnections, for example, via bus 410, can also be provided to a network interface 414, such as a network card, which can be provided to interface with a computer network, and to a media interface 416, such as a diskette or CD-ROM drive, which can be provided to interface with media 418.

A data processing system suitable for storing and/or executing program code can include at least one processor 402 coupled directly or indirectly to memory elements 404 through a system bus 410. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboard 408, display 406, pointing device, and the like) can be coupled to the system either directly (such as via bus 410) or through intervening I/O controllers (omitted for clarity).

Network adapters such as network interface 414 may also be coupled to the system to enable the data processing system to become coupled to other data processing systems or remote printers or storage devices through intervening private or public networks. Modems, cable modem and Ethernet cards are just a few of the currently available types of network adapters.

As used herein, a "server" includes a physical data processing system (for example, system 412 as shown in FIG. 4) running a server program. It will be understood that such a physical server may or may not include a display and keyboard.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method, comprising:
   positioning a measurement platform at a first location of a given water system, wherein the measurement platform comprises a first plurality of sensor devices distributed over a predetermined three dimensional space on the measurement platform and configured to acquire data relating to one or more physical properties of the water system, and wherein the measurement platform comprises a plurality of three-dimensional quadrilaterals stacked on each other including the first plurality of sensor devices at vertices of the three-dimensional quadrilaterals;
   acquiring a first set of measurement data from the water system at the first location via at least a portion of the first plurality of sensor devices of the measurement platform;
   moving the measurement platform along a predetermined path to at least a second location in the water system;
   acquiring at least a second set of measurement data from the water system at the second location via at least a portion of the first plurality of sensor devices of the measurement platform; and
   determining locations of the measurement platform at each of the first and second locations by localization using at least one of a second plurality of sensor devices positioned at an edge of the given water system and a global positioning system (GPS);
   tracking temporal variation of the given water system using a plurality of stationary sensor devices;
   determining, based on changes in values obtained by the plurality of stationary sensor devices, invalidity of a baseline model representative of one or more physical properties of the given water system; and
   updating the baseline model based on the temporal variation, wherein the updating comprises using the changes in the values and locations of the plurality of stationary sensor devices as boundary conditions to interpolate the changes across an entirety of the given water system.

2. The method of claim 1, further comprising generating an image based on the first set of measurement data and the at least a second set of measurement data, wherein the image represents the one or more physical properties of the water system.

3. The method of claim 1, further comprising utilizing at least a portion of the first set of measurement data and the at least a second set of measurement data to update a model representative of one or more physical properties of the water system.

4. The method of claim 1, further comprising interpolating data representative of one or more physical properties of the water system based on at least a portion of the first set of measurement data and the at least a second set of measurement data.

5. The method of claim 1, wherein the measurement platform is attached to a vehicle that traverses the water system along the predetermined path.

6. The method of claim 1, further comprising transmitting the first set of measurement data and the at least a second set of measurement data to a computer system.

7. The method of claim 1, further comprising moving the measurement platform to variable depth locations in the water system to acquire measurement data.

8. The method of claim 1, further comprising utilizing at least a portion of the first set of measurement data and the at least a second set of measurement data to determine at least one of a temporal variation and a spatial variation in the water system.

9. The method of claim 1, wherein the first plurality of sensor devices comprises one or more of a pH sensor, a conductivity sensor, a dissolved oxygen sensor, a temperature sensor, a turbidity sensor, an oxygen content sensor, a nitric oxide sensor, and a phosphorus sensor.

10. An apparatus, comprising:
    a frame structure;
    a first plurality of sensor devices distributed on the frame structure over a predetermined three dimensional space and configured to acquire data relating to one or more physical properties of a given water system, the frame structure and the first plurality of sensor devices forming a measurement platform, wherein the frame structure comprises a plurality of three-dimensional quadrilaterals stacked on each other including the first plurality of sensor devices at vertices of the three-dimensional quadrilaterals;
    wherein the measurement platform is configured to: (i) be positioned at a first location of the water system; (ii) acquire a first set of measurement data from the water system at the first location via at least a portion of the first plurality of sensor devices, (iii) be moved along a predetermined path to at least a second location in the given water system; and (iv) acquire at least a second set of measurement data from the water system at the second location via at least a portion of the first plurality of sensor devices; and
    wherein locations of the measurement platform at each of the first and second locations are determined by localization using at least one of a second plurality of sensor devices positioned at an edge of the given water system and a global positioning system (GPS); and
    a computer system for:
    tracking temporal variation of the given water system using a plurality of stationary sensor devices;
    determining, based on changes in values obtained by the plurality of stationary sensor devices, invalidity of a baseline model representative of one or more physical properties of the given water system; and updating the baseline model based on the temporal variation, wherein the updating comprises using the changes in the values and locations of the plurality of stationary sensor devices as boundary conditions to interpolate the changes across an entirety of the given water system.

11. The apparatus of claim 10, further comprising a computer system for generating an image based on the first set of measurement data and the at least a second set of measurement data, wherein the image represents the one or more physical properties of the given water system.

12. The apparatus of claim 10, further comprising a computer system for utilizing at least a portion of the first set of measurement data and the at least a second set of measurement data to update a model representative of one or more physical properties of the given water system.

13. The apparatus of claim 10, further comprising a computer system for interpolating data representative of one or more physical properties of the given water system based on at least a portion of the first set of measurement data and the at least a second set of measurement data.

14. The apparatus of claim 10, wherein the measurement platform is attached to a vehicle that traverses the water system along the predetermined path.

15. The apparatus of claim 10, wherein at least a portion of the first plurality of sensor devices are configured to transmit the first set of measurement data and the at least a second set of measurement data to a computer system.

16. The apparatus of claim 10, wherein the measurement platform is movable to variable depth locations in the water system to acquire measurement data.

17. The apparatus of claim 10, further comprising a computer system for utilizing at least a portion of the first set of measurement data and the at least a second set of measurement data to determine at least one of a temporal variation and a spatial variation in the given water system.

18. The apparatus of claim 10, wherein the first plurality of sensor devices comprises one or more of a pH sensor, a conductivity sensor, a dissolved oxygen sensor, a temperature sensor, a turbidity sensor, an oxygen content sensor, a nitric oxide sensor, and a phosphorus sensor.

19. An article of manufacture comprising a computer readable storage medium having tangibly embodied thereon computer readable program code which, when executed, causes a processor device to:

obtain a first set of measurement data from a given water system acquired at a first location via a measurement platform, wherein the measurement platform is positioned at the first location of the water system and comprises a first plurality of sensor devices distributed over a predetermined three dimensional space on the measurement platform and configured to acquire data relating to one or more physical properties of the water system, and wherein the measurement platform comprises a plurality of three-dimensional quadrilaterals stacked on each other including the first plurality of sensor devices at vertices of the three-dimensional quadrilaterals;

obtain at least a second set of measurement data from the water system at a second location via at least a portion of the first plurality of sensor devices of the measurement platform, wherein the measurement platform is moved along a predetermined path to the at least a second location in the water system;

determine locations of the measurement platform at each of the first and second locations by localization using at least one of a second plurality of sensor devices positioned at an edge of the given water system and a global positioning system (GPS);

generate an image based on the first set of measurement data and the at least a second set of measurement data, wherein the image represents the one or more physical properties of the water system;

track temporal variation of the given water system using a plurality of stationary sensor devices;

determine, based on changes in values obtained by the plurality of stationary sensor devices, invalidity of a baseline model representative of one or more physical properties of the given water system; and update the baseline model based on the temporal variation, wherein the updating comprises using the changes in the values and locations of the plurality of stationary sensor devices as boundary conditions to interpolate the changes across an entirety of the given water system.

20. The article of claim 19, wherein the computer readable program code which, when executed, further causes the processor device to utilize at least a portion of the first set of measurement data and the at least a second set of measurement data to update a model representative of one or more physical properties of the water system.

21. The article of claim 19, wherein the computer readable program code which, when executed, further causes the processor device to interpolate data representative of one or more physical properties of the water system based on at least a portion of the first set of measurement data and the at least a second set of measurement data.

22. The article of claim 19, wherein the computer readable program code which, when executed, further causes the processor device to utilize at least a portion of the first set of measurement data and the at least a second set of measurement data to determine at least one of a temporal variation and a spatial variation in the water system.

* * * * *